(12) United States Patent
Coffin et al.

(10) Patent No.: US 7,262,033 B1
(45) Date of Patent: Aug. 28, 2007

(54) CELL LINES FOR THE PROPAGATION OF MUTATED HERPES VIRUSES

(75) Inventors: Robert Stuart Coffin, London (GB); David Seymour Latchman, London (GB)

(73) Assignee: Biovex Limited, Oxford (GB)

( * ) Notice: Subject to any disclaimer, the term of this patent is extended or adjusted under 35 U.S.C. 154(b) by 1156 days.

(21) Appl. No.: 09/762,098

(22) PCT Filed: Aug. 3, 1999

(86) PCT No.: PCT/GB99/02547

§ 371 (c)(1),
(2), (4) Date: Jun. 20, 2001

(87) PCT Pub. No.: WO00/08194

PCT Pub. Date: Feb. 17, 2000

(30) Foreign Application Priority Data

Aug. 3, 1998 (GB) .................................. 9816856.0

(51) Int. Cl.
*C12N 15/869* (2006.01)
*C12N 15/36* (2006.01)

(52) U.S. Cl. .................................. 435/91.4; 435/320.1
(58) Field of Classification Search ............. 435/320.1, 435/441, 455, 471, 91.4; 424/229.1, 231.1
See application file for complete search history.

(56) References Cited

FOREIGN PATENT DOCUMENTS

| WO | WO96/04395 | | 2/1996 |
| WO | WO97 36481 A | | 10/1997 |
| WO | WO98 04726 A | | 2/1998 |
| WO | WO98/15637 A1 | * | 4/1998 |

OTHER PUBLICATIONS

Elliott et al. Virology. 1995, vol. 213, pp. 258-262.*
Johnson et al. J. Virol. 1994, vol. 68, pp. 6347-6362.*
Elliott J. Virol. 1994, vol. 68, pp. 4890-4897.*
Illustrated Dictiinary of Immunology, edited by Cruse et al. 1994, CRC Press Inc.*
Smiley, et al., Truncation of the C-Terminal Acidic Transcriptional Activation Domain of Herpes Simplex Virus VP16 Produces a Phenotype Similar to That of the in 1814 Linker Insertion Mutation, 1997, J. Virol., 71: 6191-6193.
Soriano, et al., Targeted Disruption of the c-src Proto-Oncogene Leads to Osteopetrosis in Mice, 1991, Cell 64: 693-702.
Weinheimer et al, "Deletion of the VP16 Open Reading Frame of Herpes Simplex Virus Type 1", Journal of Virology, 1992 vol. 66, No. 1, pp. 258-269.
Lachman et al, "The Use of Herpes Simplex Virus-Based Vectors for Gene Delivery to the Nervous System", Molecular Medicine Today, Sep. 1997, pp. 404-411.
Thomas et al, "Equine Herpesvirus 1 Gene 12 Can Substitute for vmw65 in the Growth of Herpes Simplex Virus (HSV) Type 1, Allowing the Generation of Optimized Cell Lines for the Propagation of HSV Vectors with Multiple Immediate-Early Gene Defects", Journal of Virology, vol. 73, No. 9, Sep. 1999.
Purewal et al., Equid Herpesviruses 1 and 4 Encode Functional Homologs of the Herpes Simplex Virus Type 1 Virion Transactivator Protein, VP16, 1994, Virology 198: 385-389.
Ace, et al., Mutational Analysis of the Herpes Simplex Virus Type 1 Trans-inducing Factor Vmw65, 1988, J. Gen. Virol., 69: 2595-2605.
Ace, et al., Construction and Characterization of a Herpes Simplex Virus Type 1 Mutant Unable To Transinduce Immediate-Early Gene Expression, 1989, J. Virol., 63: 2260-2269.
Chou, et al.,Differential Response of Human Cells to Deletions and Stop Codons in the $y_1 34.5$ Gene of Herpes Simplex Virus, 1994, J. Virol. 68: 8304-8311.
Chou, et al., The $y_1 34.5$ Gene of Herpes Simplex Virus 1 Precludes Neuroblastoma Cells from Triggering Total Shutoff of Protein Synthesis Characteristic of Programmed Cell Death in Neuronal Cells, PNAS 89: 3266-3270, (1992).
Coffin, et al., In: Genetic Manipulation of the Nervous System, 1996, Proc. Natl. Acad. Sci. USA, pp. 99-114.
Coffin, et al., Gene Delivery to the Central and Peripheral Nervous Systems of Mice Using HSV1 ICP34.5 Deletion Mutant Vectors, 1996, Gene Therapy, 3, 886-891.
DeLuca, et al., Isolation and Characterization of Deletion Mutants of Herpes Simplex Virus Type 1 in the Gene Encoding Immediate-Early Regulatory Protein ICP4, 1985, J. Virol., 56: 558-570.
Gelman, et al., Herpes Simplex Virus Immediate-Early Promoters are Responsive to Virus and Cell trans-Acting Factors, 1987, J. Virol., 61, 2286-2296.
Howard, et al., High Efficiency Gene Transfer to the Central Nervous System of Rodents and Primates Using Herpes Virus Vectors Lacking Functional ICP27 and ICP34.5, 1998, Gene Therapy 5: 1137-1147.

(Continued)

Primary Examiner—Bruce R. Campell
Assistant Examiner—Bao Qun Li
(74) *Attorney, Agent, or Firm*—Nixon & Vanderhye P.C.

(57) ABSTRACT

A process for propagating a mutant herpes virus having a mutation in its endogenous HSV VP16 gene or a homologue thereof, which process comprises infecting a cell line with the mutant herpes virus and culturing the cell line, wherein the cell line comprises a nucleic acid sequence encoding a functional herpes simplex virus (HSV) VP16 polypeptide, or a homologue thereof, operably linked to a control sequence permitting expression of the polypeptide in said cell line; the nucleic acid sequence being (i) capable of complementing the endogenous gene and (ii) unable to undergo homologous recombination with the endogenous gene. In addition, the present invention provides cell lines which can be used for the growth of mutant herpes viruses which have defects in certain immediate early genes together with mutations in VP16 or homologue thereof.

13 Claims, No Drawings

OTHER PUBLICATIONS

Liewis, et al., Structural and Antigenic Identification of the oRF12 Protein (αTIF) of Equine Herpesvirus, 1997, Virology, 230, 369-375.

Lokensgard, et al., Long-Term Promoter Activity during Herpes Simplex Virus Latency, 1994, J. Virol. 68, 7148-7158.

MacLean, et al., Herpes Simplex Virus Type 1 Deletion Variants 1714 and 1716 Pinpoint Neurovirulence-Related Sequences in Glasgow Strain 17[+] Between Immediate Early Gene 1 and the 'a' Sequence, 1991, J. Gen. Virol. 72: 632-639.

McFarlane, et al., Hexamethylene Bisacetamide Stimulates Herpes Simplex Virus Immediate Early Gene Expression in the Absence of Trans-induction by Vmw65, 1992, J. Gen. Virol., 73, 285-292.

Misra, et al., Protein and DNA Elements Involved in Transactivation of the Promoter of the Bovine Herpesvirus (BHV) 1 IE-1 Transcription Unit by the BHV α Gene trans-Inducing Factor, 1994, J. Virol., 68, 4898-4909.

Moriuchi, et al., Varicella-Zoster Virus Open Reading Frame 10 Protein, the Herpes Simplex Virus VP16 Homolog, Transactivates Herpesvirus Immediate-Early Gene Promoters, 1993, J. Virol. 67, 2739-2746.

Moriuchi, et al., Proteins and cis-Acting Elements Associated with Transactivation on the Varicella-Zoster Virus (VZV) Immediate-Early Gene 62 Promoter by VZV Open Reading Frame 10 Protein, 1995, J. Virol., 69, 4693-4701.

Rice, et al., Genetic Evidence for Two Distinct Transactivation Functions of the Herpes Simplex Virus α Protein ICP27, 1990, J. Virol. 64: 1704-1715.

Roizman, et al., Herpes Simplex Viruses and Their Replication, 1996, Fundamental Virology, 1043-1107.

Samaniego, et al., Functional Interactions between Herpes Simplex Virus Immediate-Early Proteins during Infection: Gene Expression as a Consequence of ICP27 and Different Domains of ICP4, 1995, J. Virol., 69: 5705-5715.

Sekulovich, et al., The Herpes Simplex Virus Type 1 α Protein ICP27 Can Act as a trans-Repressor or a trans-Activator in Combination with ICP4 and ICP0, 1988, J. Virol., 62: 4510-4522.

\* cited by examiner

CELL LINES FOR THE PROPAGATION OF MUTATED HERPES VIRUSES

The present application is a 371 U.S. National Phase of Application No. PCT/GB99/02547, filed 3 Aug. 1999, which designated the U.S.

FIELD OF THE INVENTION

The present invention relates to cell lines used for the growth of mutant herpes viruses. It particularly relates to the growth of viruses with mutations in genes which are essential structural proteins, but which also have other functions the inactivation of which impairs virus growth. The invention provides cell lines giving enhanced growth of viruses with such inactivating mutations in a manner in which the inactivated function in the virus cannot be repaired by homologous recombination of viral sequences with the complementing sequences in the cell line. In addition, the present invention also provides cell lines which can be used for the growth of mutant herpes viruses which have defects in certain immediate early genes together with mutations in the essential structural protein.

BACKGROUND TO THE INVENTION

Herpes viruses have been suggested as potential vectors for gene delivery. This could, for example, either be to the nervous system or elsewhere in the body for gene therapy, vaccine or other purposes, or to cells in culture or to animal models of disease. However, while HSV has a number of potential advantages as a vector in that it can infect a wide variety of cell types in vitro and in vivo and can accept large DNA insertions allowing the delivery of multiple genes, infection of most cell types with HSV will result in lytic replication or other toxic effects of the virus. Thus for use as a vector HSV must usually be disabled in some way to prevent or minimise these effects.

HSV can be disabled in a number of ways, and this includes when used as a helper virus in the growth of so-called amplicon vectors which consist of plasmids containing herpes origin and packaging sequences which can be replicated in the presence of a helper virus after transfection into permissive cells. For example genes required for replication in all cell types can be inactivated, which must be complemented for growth in culture, these including one or other or both of the essential immediate early genes ICP4 or ICP27. Alternatively genes required for pathogenesis in vivo but which are not required for growth in culture can be removed, such as ICP34.5 or ICP6, as can further genes the deletion of which reduces toxicity further. These can for example include the other IE genes ICPO, ICP22, and ICP47, the inactivation of ICPO and/or ICP22 reducing the efficiency of virus replication in culture unless these are also complemented in the cell line used for virus growth. The production of effective and practical vector viruses therefore depends on a balance of appropriately minimised toxicity in the target cell type, and on the ability to grow the virus in culture, in some cases requiring the use of a cell line complementing at least some of the inactivating mutations in the virus. As a general rule, the greater the number of mutations in the virus, the harder the virus will be to grow in culture. HSV vectors generally are reviewed in Coffin and Latchman, 1996.

It can be seen from the above that particularly attractive genes for inactivation in the production of HSV vectors are one or more of the five IE genes, as inactivation of these will for ICPO, ICP4, ICP22 or ICP27 at least, also reduce levels of other proteins the expression of which is stimulated by these IE gene products. However if these genes are inactivated replication in culture will either be blocked (ICP4 and ICP27) or reduced (ICPO and ICP22), and thus for efficient replication the inactivated genes must be complemented in the cell line used for virus growth.

However an alternative means by which the levels of functional IE proteins can be reduced, rather than by including inactivating mutations in the IE genes themselves, is to include an inactivating mutation in the gene encoding VP 16 (Ace et al., 1988). VP 16 is a virion protein that together with cellular factors is responsible for the trans-activation of HSV IE gene promoters after infection. Thus inclusion of specific inactivating mutations in VP 16 results in a virus in which IE gene expression is reduced, although not blocked completely (Ace et al., 1989). This may be advantageous in the production of an HSV vector virus as inactivation of a function in one gene (VP16) results in reduced levels of expression of multiple IE genes.

The gene for VP 16 cannot however be deleted from the virus as it is also an essential structural protein. Specific mutations are therefore used which reduce or abolish the transactivating activity of VP 16, but still allow the protein to fulfill its structural function (Ace et al., 1988). Viruses including this type of mutation—specifically insertion of a linker sequence into the gene for VP 16 as in virus mutant in1814 (Ace et al., 1989)—are essentially avirulent in vivo, giving reduced growth both in vivo and in culture (Ace et al., 1989). Growth of stocks of viruses including such a mutation is thus of reduced efficiency as compared to viruses lacking the mutation. The mutation in VP16 can be partially compensated for by the inclusion of HMBA in the media (MacFarlane et al., 1992), but cell lines cannot be used that have been engineered to express an unaltered copy of VP 16 without the generation of virus in the culture in which the mutation has been repaired. This is because, as the gene cannot be deleted from the virus due to its essential structural role, the inclusion of an unaltered copy of the gene for VP 16 in the cell line used for virus growth would result in the generation of virus containing the unaltered VP 16 sequence by homologous recombination between the mutated VP16 sequence in the virus and the unaltered VP16 sequence in the cell line. Moreover complementation of the VP16 mutation by such a cell line would in any case result in the production of new virions containing fully functional VP16, which when used as a vector in non-complementing cells would activate IE gene expression, exactly as the mutation in VP16 was intended to reduce.

The problem therefore remains of how to efficiently grow stocks of HSV including mutations in the gene for VP16 which affect the trans-activating properties of the protein, such that the mutation in the virus cannot be repaired during virus growth.

SUMMARY OF THE INVENTION

HSV with mutations in VP 16 that reduce the trans-activating properties of the protein may be particularly attractive as vectors, particularly when combined with inactivating mutations in other HSV genes (see Coffin and Latchman, 1996). However such viruses cannot easily be efficiently grown in culture without repair of the mutation if a cell line complementing VP16 is used (see above). The main function of VP16, as well as its structural role, is to trans-activate HSV IE promoters after infection. We have found that not only can a protein with a similar role in another herpes virus, equine herpes virus 1 (EHV 1), transactivate HSV IE promoters, but that it can also greatly enhance the growth of HSV with mutations in VP 16 when stably transfected into the cells used for virus growth. There is little nucleotide sequence similarity between the EHV 1 equivalent of VP16 (Gene 12; see Lewis et al., 1997, here termed EHV-VP16) and HSV-VP16, and thus homologous recombination repairing the mutation in the virus is not possible. The invention thus for the first time provides cell lines which allow the efficient growth of HSV with mutations in VP16, reducing its transactivating properties, but in which repair of the mutation by homologous recombination is not possible.

The invention also provides a general methodology by which mutations in genes encoding essential structural polypeptides in HSV or homologous genes in other viruses can be complemented for growth in culture by the use of a protein with a homologous function in one virus to complement a deficiency in the equivalent protein in another. For example, HSV mutations in VP16 may be complemented using the EHV-VP16 equivalent (as here) or the homologous protein from another herpes virus, e.g. BTIF from bovine herpes virus (BHV; Misra et al., 1994), or the ORF10 gene product from varicella zoster virus (VZV; Moriuchi et al., 1993).

Accordingly, the present invention provides a process for propagating a mutant herpes virus having a mutation in its endogenous HSV VP 16 gene or a homologue thereof, which process comprises infecting a cell line with the mutant herpes virus and culturing the cell line, wherein the cell line comprises a nucleic acid sequence encoding a functional herpes simplex virus (HSV) VP 16 polypeptide, or a homologue thereof, operably linked to a control sequence permitting expression of the polypeptide in said cell line; the nucleic acid sequence being (i) capable of complementing the endogenous gene and (ii) unable to recombine with the endogenous gene.

Preferably the mutation is a mutation which reduces or abolishes the ability of said endogenous gene to activate viral transcription Preferably, the functional HSV VP 16 homologue is encoded by a herpes virus gene, more preferably an equine herpes virus gene, for example gene 12, or a bovine herpes virus gene, for example BTIF. The mutant herpes virus is preferably a herpes simplex virus (HSV) more preferably an HSV-1 or HSV-2 virus or a derivative thereof.

The mutant herpes virus may also comprise additional mutations which functionally inactivate additional genes of the virus and which need to be complemented by the cell line to allow viral growth in the cell line. In this case, the cell line will comprise additional nucleic acid sequences encoding functional herpes virus genes that complement the endogenous genes that have been functionally inactivated. For example, in a preferred embodiment, the mutant virus is a herpes simplex virus lacking functional essential immediate early genes such as ICP4 and/or ICP27. Consequently, the cell line of the invention will also comprise a functional ICP4 and/or ICP27 gene, as appropriate, to provide functional ICP4 and/or ICP27 thus allowing growth of the disabled virus in culture.

In particularly preferred embodiments the gene(s) for ICP4 and/or ICP27 are deleted from an HSV mutant also having the in 1814 inactivating mutation in VP 16 (Ace et al., 1989). These mutants are grown on cell lines containing the EHV-VP 16 gene and also the ICP4 and/or ICP27 genes, but with no overlap between the sequences inserted into the cell line and those remaining in the virus. This prevents repair of any of the mutations in the virus by homologous recombination between sequences in the cell line and in the virus during virus growth. The inventors have found that in such embodiments promoter choice driving expression of ICP4 and ICP27 in the cells is important of the reliable generation of complementing cells containing EHV-VP16 and/or ICP27. The current invention thus also provides cell lines in which such promoter choice has been optimised. In such embodiments it is preferred that ICP27 gene expression is driven by the ICP27 promoter and that ICP4 gene expression is driven by the ICP4 promoter or more preferably by the MMTV LTR promoter.

The mutant herpes viruses produced by the process of the invention may be isolated from the cultured cell line and, optionally, further purified. The viruses may also be formulated as a pharmaceutical composition with a pharmaceutically acceptable carrier or diluent.

The present invention also provides a cell line comprising a nucleic acid sequence encoding a functional herpes simplex virus (HSV) VP 16 polypeptide homologue, operably linked to a control sequence permitting expression of the polypeptide in said cell line, which nucleic acid sequence is (i) capable of complementing an HSV VP16 gene and (ii) unable to recombine with the HSV VP16 gene.

Preferably, the functional HSV VP 16 homologue is encoded by a herpes virus gene, more preferably an equine herpes virus gene, for example gene 12, or a bovine herpes virus gene, for example BTIF. The mutant herpes virus is preferably a herpes simplex virus (HSV) more preferably an HSV-1 or HSV-2 virus or a derivative thereof.

Cell lines may also be produced in which other genes inactivated in the virus are complemented in the cell line for virus growth, together with (in the case of HSV) complementation of inactivating mutations in the gene for VP 16 using the VP 16 equivalent from another herpes virus. For example if either ICP4 and/or ICP27 are inactivated cell lines also containing ICP4 and/or ICP27 may be used. In this embodiment promoter choice driving expression of ICP4 and ICP27 in the cells is important, the current invention thus also provides cell lines in which such promoter choice has been optimised. A preferred promoter for driving ICP27 gene expression in the ICP27 promoter and preferred promoters for driving ICP4 gene expression include the MMTV LTR and ICP4 promoters.

DETAILED DESCRIPTION OF THE INVENTION

A. Herpes Viruses

Herpes viruses include any virus that is a member of the family herpesviridae. This includes equine herpes virus, bovine herpes virus and the human herpes simplex virus group, in particular HSV1 and HSV2.

When the virus of the invention is a herpes simplex virus, the virus may be derived from, for example, HSV1 or HSV2 strains, or derivatives thereof, preferably HSV1. Derivatives include inter-type recombinants containing DNA from HSV1 and HSV2 strains. Derivatives preferably have at least 70% sequence homology to either the HSV1 or HSV2 genomes, more preferably at least 80%, even more preferably at least 90 or 95%. Other derivatives which may be used to obtain the viruses of the present invention include strains that already have mutations in genes, particularly mutations in genes that result in attenuation of the virus. Examples of such viruses include strain 1716 (MacLean et al., 1991), strains R3616 and R4009 (Chou and Roizman, 1992) and R930 (Chou et al., 1994) all of which have mutations in ICP34.5, strain d120 which has a deletion in ICP4 (DeLuca et al., 1985), strain d27-1 (Rice and Knipe, 1990) which has a deletion in ICP27) or strain d92 which has deletions in both ICP27 and ICP4 (Samaniego et al., 1995).

The terminology used in describing the various HSV genes is as found in Coffin and Latchman, 1996.

B. Mutations in Structural Genes

A mutant herpes virus in the context of the present invention typically has a mutation in a gene encoding an essential structural polypeptide that has a secondary non-structural function, for example transcriptional activation or enzymatic activity. The mutation will affect the secondary function of the protein, typically transcriptional activation, resulting in a reduction in the efficiency of virus growth, but without preventing the expression of the polypeptide thus allowing the polypeptide to fulfil its structural role. The mutation in said structural gene typically reduces or abolishes the ability of the polypeptide encoded by the gene to activate viral transcription, in particular transcription initiated from immediate early promoters. The reduction in viral transcription mediated by the structural polypeptide is generally at least 50%, more preferably at least 70, 80, or 90%.

In a preferred embodiment of the invention, the structural gene is the HSV gene encoding VP16 (UL48), or a homologue thereof found in a different herpes virus, for example equine herpes virus gene 12 or bovine herpes virus gene BTIF. The HSV VP16 gene typically has an insertion that abolishes its trans-activating ability (see, for example, Ace et al., 1989). Other mutants with similar properties have also been described including a truncation of the acidic activation domain of HSV VP16 (e.g. see Smiley, J. R., and J. Duncan. 1997). Such mutants are also suitable for use in the invention.

By a "homologue" it is meant a virus gene that exhibits sequence homology, at the amino acid level, to the corresponding structural herpes virus gene which is mutated in the mutant herpes virus which it is desired to propagate. Typically, a homologue of, for example, an HSV gene will be at least 15%, preferably at least 20%, identical at the amino acid level to the corresponding HSV gene over a region of at least 20, preferably at least 30, for instance at least 40, 60 or 100 or more contiguous amino acids. The homologue must be capable of complementing the function of the mutant endogenous gene present in the genome of the mutant herpes virus that it is desired to propagate. However, to avoid homologous recombination between the functional structural herpes virus gene present in the complementing cell line and the mutant gene present in the herpes virus genome, the functional gene should be no more than 50%, preferably no more than 40 or 30% identical at the nucleotide level, over the entire coding sequence to the corresponding mutant gene present in the herpes virus.

Methods of measuring protein and nucleotide homology are well known in the art and it will be understood by those of skill in the art that in the present context, protein homology is calculated on the basis of amino acid identity (sometimes referred to as "hard homology").

Methods of measuring nucleic acid and protein homology are well known in the art. Homology can be calculated using, for example, the UWGCG Package which provides the BESTFIT program which can be used to calculate homology (Devereux et al (1984) *Nucleic Acids Research* 12, p. 387-395). Similarly, the PILEUP and BLAST algorithms can be used to line up sequences (for example as described in Altschul S. F. (1993) *J. Mol. Evol.* 36:290-300; Altschul, S. F. et al (1990) *J. Mol. Biol.* 215:403-10). Many different settings are possible for such programs. According to the invention, the default settings may be used.

Further, the sequence of the functional structural gene may be modified at the nucleotide level, for example by substitution, to reduce the degree of homology between the functional gene present in the cell line and the mutant gene present in the herpes virus to reduce further the possibility of recombination. This can be achieved without changing the amino acid sequence of the functional gene as a result of the degeneracy of the genetic code.

Conservative substitutions may also be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Homologues of herpes virus genes from particular herpes viruses (for example HSV) can be identified in other viruses in a number of ways, for example by probing genomic or cDNA libraries made from other viruses with probes comprising all or part of the HSV gene under conditions of medium to high stringency (0.2×SSC/0.1% SDS at from about 40° C. to about 55° C.). Alternatively, species homologues may also be obtained using degenerate PCR which will use primers designed to target sequences within the variants and homologues encoding conserved amino acid sequences. The primers will contain one or more degenerate positions and will be used at stringency conditions lower than those used for cloning sequences with single sequence primers against known sequences (for example, 2×SSC at 60° C.).

In the case of HSV1 and HSV2 such strains particularly include mutations in the gene for VP 16 (UL48) which abolish or reduce the trans-activating activity of the protein without affecting its structural role (see, for example, Ace et al., 1988). These virus strains also include strains in which further mutations have been included, possibly requiring the use of cell lines also complementing these mutations e.g. ICP4 and/or ICP27 for HSV1 or their functional equivalents in HSV2, if one or other or both of these genes contain inactivating mutations. Preferred viruses include HSV1 or HSV2 containing mutations abolishing the transactivating function of VP16, together with the complete deletion of the genes for ICP4 and/or ICP27 (or equivalents in HSV2) such that there is no overlap between the DNA remaining in the virus and that in the cell line used for virus growth. Further inactivating mutations may also be made in the virus, for example in ICP34.5, vhs, and/or ICP6. A particularly preferred virus would include inactivating mutations in all of these genes.

The various other viral genes referred to may be rendered functionally inactive by several techniques well known in the art. For example, they may be rendered functionally inactive by deletions, substitutions or insertions, preferably by deletion. Deletions may remove portions of the genes or the entire gene. For example, deletion of only one nucleotide may be made, resulting in a frame shift. However, preferably larger deletions are made, for example at least 25%, more preferably at least 50% of the total coding and non-coding sequence (or alternatively, in absolute terms, at least 10 nucleotides, more preferably at least 100 nucleotides, most preferably, at least 1000 nucleotides). It is particularly preferred to remove the entire gene and some of the flanking sequences. Inserted sequences may include the heterologous genes described below. In particular, it is preferred to insert the heterologous gene into ICP4.

In the case of the gene encoding an essential structural polypeptide, clearly it is not desirable to delete large portions of the gene. However, small deletions, insertions and/or substitutions may be made as appropriate to abrogate the desired activity, for example trans-activation (see, for example, Ace et al., 1989).

Mutations are made in the herpes viruses by homologous recombination methods well known to those skilled in the art. For example, HSV genomic DNA is transfected together with a vector, preferably a plasmid vector, comprising the mutated sequence flanked by homologous HSV sequences. The mutated sequence may comprise deletions, insertions or substitutions, all of which may be constructed by routine techniques. Insertions may include selectable marker genes, for example lacZ, for screening recombinant viruses by, for example, β-galactosidase activity.

C. Heterologous Genes and Promoters

The viruses of the invention may carry a heterologous gene. The term "heterologous gene" encompasses any gene. Although a heterologous gene is typically a gene not present in the genome of a herpes virus, a herpes gene may be used provided that the coding sequence is not operably linked to the viral control sequences with which it is naturally associated. The heterologous gene may be any allelic variant of a wild-type gene, or it may be a mutant gene. The term "gene" is intended to cover nucleic acid sequences which are capable of being at least transcribed. Thus, sequences encoding mRNA, tRNA and rRNA are included within this definition. Nucleic acids may be, for example, ribonucleic acid (RNA) or deoxyribonucleic acid (DNA) or analogues thereof. Sequences encoding mRNA will optionally include some or all of 5' and/or 3' transcribed but untranslated flanking sequences naturally, or otherwise, associated with the translated coding sequence. It may optionally further include the associated transcriptional control sequences normally associated with the transcribed sequences, for example transcriptional stop signals, polyadenylation sites and downstream enhancer elements.

The heterologous gene may be inserted into the viral genome by homologous recombination of HSV strains with, for example, plasmid vectors carrying the heterologous gene flanked by HSV sequences. The heterologous gene may be introduced into a suitable plasmid vector comprising herpes viral sequences using cloning techniques well-known in the art. The heterologous gene may be inserted into the viral genome at any location provided that the virus can still be propagated. It is preferred that the heterologous gene is inserted into an essential gene.

The transcribed sequence of the heterologous gene is preferably operably linked to a control sequence permitting expression of the heterologous gene in mammalian cells, preferably cells of the central and peripheral nervous system. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

The control sequence comprises a promoter allowing expression of the heterologous gene and a signal for termination of transcription. The promoter is selected from promoters which are functional in mammalian, preferably human, cells. The promoter may be derived from promoter sequences of eukaryotic genes. For example, it may be a promoter derived from the genome of a cell in which expression of the heterologous gene is to occur, preferably a cell of the mammalian central or peripheral nervous system. With respect to eukaryotic promoters, they may be promoters that function in a ubiquitous manner (such as promoters of α-actin, tubulin) or, alternatively, a tissue-specific manner (such as promoters of the genes for pyruvate kinase). Promoters that are active in only certain neuronal cell types are especially preferred (for example the tyrosine hydroxylase (TH), L7, or neuron specific enolase (NSE) promoters). They may also be promoters that respond to specific stimuli, for example promoters that bind steroid hormone receptors. Viral promoters may also be used, for example the Moloney murine leukemia virus long terminal repeat (MMLV LTR), the promoter rous sarcoma virus (RSV) LTR promoter or the human cytomegalovirus (CMV) IE promoter.

The HSV LAT promoter, and promoters containing elements of the LAT promoter region, may be especially preferred because there is the possibility of achieving long-term expression of heterologous genes during latency. In particular, an expression cassette consisting essentially of a LAT P2 region, which does not itself here act as a promoter, linked to a promoter and a heterologous gene in that order is especially preferred (WO98/30707).

The term "long-term expression" is taken to mean expression of a heterologous gene in a cell infected with a herpes simplex virus of the invention even after the herpes simplex virus has entered latency. Preferably, this is for at least two weeks, more preferably at least one or two months after infection, even more preferably for the life-time of the cell.

Expression cassettes may further comprise a second promoter and a second heterologous gene operably linked in that order to said HSV LAT P2 region and in the opposite orientation to the first promoter and first heterologous gene wherein said second promoter and second heterologous gene are the same as or different to the first promoter and first heterologous gene. Thus a pair of promoter/heterologous gene constructs in opposite orientations flank a single LAT P2 region allowing the long term expression of pairs of heterologous genes, which may be the same or different, driven by the same or different promoters. Furthermore, the product of the first heterologous gene may regulate the expression of the second heterologous gene (or vice-versa) under suitable physiological conditions.

Expression cassettes and other suitable constructs comprising the heterologous gene and control sequences can be made using routine cloning techniques known to persons skilled in the art (see, for example, Sambrook et al., 1989, Molecular Cloning—a laboratory manual; Cold Spring Harbor Press). The LAT P2 region is here defined as HSV 1 nucleotides 118866-120219 of HSV I strain 17+(GenBank HE 1 CG: from PstI-BstXI sites), fragments or derivatives of this region, including homologous regions of other HSV 1 strains and of HSV2, which are capable of providing a long-term expression capability to promoters to which they are linked.

It may also be advantageous for the promoters to be inducible so that the levels of expression of the heterologous gene can be regulated during the life-time of the cell. Inducible means that the levels of expression obtained using the promoter can be regulated. For example, in a preferred embodiment where more than one heterologous gene is inserted into the HSV genome, one promoter would comprise a promoter responsive to the tet repressor/VP16 transcriptional activator fusion protein, and driving the heterologous gene the expression of which is to be regulated. The second promoter would comprise a strong promoter (e.g. the CMV IE promoter) driving the expression of the tet repressor/VP 16 fusion protein. Thus in this example expression of the first heterologous gene would depend on the presence or absence of tetracycline.

In addition, any of these promoters may be modified by the addition of further regulatory sequences, for example enhancer sequences (including elements of the LAT region). Chimeric promoters may also be used comprising sequence elements from two or more different promoters described above, for example an MMLV LTR/LAT fusion promoter (Lokensgard et al., 1994) or promoters comprising elements of the LAT region (see above).

The heterologous gene may encode, for example, proteins involved in the regulation of cell division, for example mitogenic growth factors including neurotrophic growth factors (such as brain-derived neurotrophic factor, glial cell derived neurotrophic factor, NGF, NT3, NT4 and NT5, GAP43 and), cytokines (such as α, β or γ-interferon, interleukins including IL-1, IL-2, tumour necrosis factor, or insulin-like growth factors I or II), protein kinases (such as MAP kinase), protein phosphatases and cellular receptors for any of the above. The heterologous gene may also encode enzymes involved in cellular metabolic pathways, for example enzymes involved in amino acid biosynthesis or degradation (such as tyrosine hydroxylase or GTP-cyclohydrolase), purine or pyrimidine biosynthesis or degradation, and the biosynthesis or degradation of neurotransmitters, such as dopamine, or protein involved in the regulation of such pathways, for example protein kinases and phosphatases. The heterologous gene may also encode transcription factors or proteins involved in their regulation, for example members of the Brn3 family or pocket proteins of the Rb family such as Rb or p107, membrane proteins (such as rhodopsin), structural protein (such as dystrophin) or heat shock proteins such as hsp70.

Preferably, the heterologous gene encodes a polypeptide of therapeutic use. For example, of the proteins described above, tyrosine hydroxylase and glial cell derived neurotrophic factor can be used in the treatment of Parkinson's disease, rhodopsin can be used in the treatment of eye disorders, dystrophin may be used to treat muscular dystrophy, and heat shock proteins can be used to treat disorders of the heart and brain associated with ischaemic stress. Polypeptides of therapeutic use may also include cytotoxic polypeptides such as ricin, or enzymes capable of converting a precursor prodrug into a cytotoxic compound for use in, for example, methods of virus-directed enzyme prodrug therapy or gene-directed enzyme prodrug therapy. In the latter case, it may be desirable to ensure that the enzyme has a suitable signal sequence for directing it to the cell surface, preferably a signal sequence that allows the enzyme to be exposed on the exterior of the cell surface whilst remaining anchored to cell membrane. Suitable enzymes include bacterial nitroreductase such as *E. coli* nitroreductase as disclosed in WO93/08288 or carboxypeptidase, especially carboxypeptidase CPG2 as disclosed in WO88/07378. Other enzymes may be found by reference to EP-A-415731. Suitable prodrugs include nitrogen mustard prodrugs and other compounds such as those described in WO88/07378, WO89/10140, WO90/02729 and WO93/08288 which are incorporated herein by reference.

Heterologous genes may also encode antigenic polypeptides for use as vaccines. Preferably such antigenic polypeptides are derived from pathogenic organisms, for example bacteria or viruses.

Heterologous genes may also include marker genes (for example encoding β-galactosidase or green fluorescent protein) or genes whose products regulate the expression of other genes (for example, transcriptional regulatory factors including the tet repressor/VP16 transcriptional activator fusion protein described above).

Gene therapy and other therapeutic applications may well require the administration of multiple genes. The expression of multiple genes may be advantageous for the treatment of a variety of conditions. Herpes viruses are uniquely appropriate as they do not have the limited packaging capabilities of other viral vector systems. Thus multiple heterologous genes can be accommodated within its genome. There are, for example, at least two ways in which this could be achieved. For example, more than one heterologous gene and associated control sequences could be introduced into a particular HSV strain. It would also be possible to use pairs of promoters (the same or different promoters) facing in opposite orientations away from a centrally located LAT P2 element, these promoters each driving the expression of a heterologous gene (the same or different heterologous gene) as described above.

E. Complementing Structural Genes

The nucleic acid sequence present in the cell line of the invention, which encodes a functional structural herpes virus polypeptide, will be able to complement in trans the activity of the corresponding mutated endogenous gene in the mutant herpes virus that it is desired to propagate. Typically, the functional complementing gene will be a homologue of the mutant endogenous gene. The identification of suitable homologues, where not already known, is described above. However, as discussed above, the functional structural gene must be unable to recombine by homologous recombination with the mutant endogenous gene present in the mutant virus to repair the mutant endogenous gene. Thus the level of nucleotide homology between the two genes must be such that homologous recombination can not occur between the two sequences. The appropriate level of nucleotide homology required to achieve this is described above.

The functional structural gene will therefore typically originate from a different virus to the mutant endogenous gene, such as a different viral species. Thus, for example, where the mutant herpes virus is an HSV with a mutation in its endogenous VP16 gene, the functional gene will be a homologue of VP 16 from a different virus, for example an equine herpes virus gene 12, a bovine herpes virus BTIF gene or a VZV ORF 10 gene. A particularly preferred VP16 sequence is that encoding gene 12 from EHV1 (nts 13505-14944 of the complete EHV1 genome [GenBank file HSECOMGEN]).

Equally, where it is desired to propagate an equine or bovine herpes virus which as a mutation in its endogenous gene 12 or BTIG gene, respectively, the cell line may comprise a functional HSV VP 16 coding sequence.

The coding sequence of the functional structural polypeptide is operably linked to a control sequence permitting expression of the polypeptide in a cell line of the invention.

Cell lines of the invention are typically mammalian cells and therefore the control sequences will be regulatory sequences capable of functioning in mammalian cells. The control sequences may be constitutively active in the cell line or may be inducible. Suitable control sequences are described above.

F. Cell Lines

Cell lines used in the invention include any cell line comprising a nucleic acid sequence encoding a functional structural herpes virus polypeptide, operably linked to a control sequence permitting expression of the polypeptide in the cell line. A suitable cell line is a cell line which hosts herpes viruses and forms colonies. Typically the cell line is a mammalian cell line such as a rodent or human cell line.

The functional structural herpes virus polypeptide is a polypeptide from one virus which can complement the growth of another virus in which the gene for the homologous polypeptide has been mutated. Preferred polypeptides perform an essential structural role in the virus, and also a second function the inactivation of which reduces the efficiency of virus growth. In the case of HSV1 or HSV2, preferred mutations include those of the type described by Ace et al., 1988 or Smiley and Duncan, 1997 in the gene for VP16. Preferred cell lines of the invention thus containing a gene for the functional equivalents of VP 16 from another viruses, for example gene 12 from EHV 1, BTIF from BHV, or ORF 10 from VZV.

Cell lines expressing a functional herpes virus structural polypeptide can be produced by standard methods such as co-transfecting mammalian cells, for example Vero or BHK cells, with a vector, preferably a plasmid vector, comprising a nucleic acid encoding the structural polypeptide, and a vector, preferably a plasmid vector, encoding a selectable marker, for example neomycin resistance. Clones possessing the selectable marker are then screened further to determine which clones also express functional polypeptide, for example on the basis of their ability to support the growth of VP16 mutant HSV strains, using methods known to those skilled in the art (for example as described in Rice and Knipe, 1990).

A particularly preferred cell line would be based on BHK or Vero cells, and contain the EHV1 gene 12 sequence together with the gene for ICP27 and/or ICP4 or equivalents from HSV2 allowing the propagation of HSV with an inactivating mutation in VP16, together with further inactivating mutations in the genes for ICP27 and/or ICP4. Preferably there would be no overlap between the DNA in the cell line and that remaining in the virus to be grown, preventing repair of the inactivating mutations in the virus to be grown by homologous recombination between DNA in the virus and DNA in the cell line.

Cell lines expressing ICP27 and/or ICP4 are known in the art, for example V27 cells (Rice and Knipe, 1990), B130/2 cells (WO98/30707) or used E26 cells (Samaniego et al., 1995). These cell lines may be utilised to produce a cell line of the invention. However, as we have found promoter choice driving ICP4 and ICP27 to be important in such embodiments, the current invention also provides for cell lines in which such promoter choice has been optimized, by driving ICP4 expression from the ICP4 promoter or MMLV LTR promoter and ICP27 expression from the ICP27 promoter.

The invention will be described with reference to the following Examples which are intended to be illustrative only and not limiting.

EXAMPLES

HSV-1 nucleotide numbers referred to in the following examples refer to GenBank file HE1CG.

Example 1

EHV-VP16 can Trans-Induce HSV Immediate Early Gene Promoters

CAT assays (by the method of Gorman 1985) were performed in which plasmid constructs with the chloramphenicol acetyl transferase gene under the control of either the HSV1 ICP4, ICP0 or ICP27 (pIGA102, pIGA65 and pIGA95 respectively; Gelman and Silverstein, 1987) were co-transfected into BHK cells together with either a control plasmid (pcDNA3; Invitrogen), or similar plasmids into which either HSV-VP16 (PCMV16; Moriuchi et al., 1995) or EHV-VP 16 sequences had been inserted. 51g of each plasmid was used per transfection into 6 well plates. Experiments were performed in duplicate. The EHV-VP16 expression construct (pcDNA3/E) was constructed by insertion of the EHV-VP16 sequence into the EcoRV and XbaI sites of pcDNA3 (Invitrogen) after release from pcDNA1/amp by digestion with EcoRI and XbaI into which it had originally been cloned.

RESULTS

Results are shown as the % conversion of the $^{14}$C-labelled chloramphenicol from the non-acetylted to acetylated forms by phosphorimagery of resulting TLC plates. The results of each duplicate experiment are shown.

| Test promoter | Activator | % conversion |
| --- | --- | --- |
| ICP0 | control | 31, 33 |
| ICP0 | HSV-VP16 | 83, 83 |
| ICP0 | EHV-VP16 | 82, 84 |
| ICP27 | control | 15, 16 |
| ICP27 | HSV-VP16 | 44, 38 |
| ICP27 | EHV-VP16 | 27, 34 |
| ICP4 | control | 34, 30 |
| ICP4 | HSV-VP16 | 75, 76 |
| ICP4 | EHV-VP16 | 75, 63 |

These results showed that EHV-VP 16 could trans-activate HSV 1 IE promoters to a similar degree to HSV-VP 16 for the ICP0 and ICP4 promoters, and somewhat less so for the ICP27 promoter, which is in any case less responsive to HSV-VP 16 than are the other two promoters tested. This suggested that EHV-VP 16 might functionally complement HSV-VP16 mutants such as in1814 (Ace et al., 1989) in which the trans-activating activity has been reduced, if expressed in the cells used for virus growth, providing cell lines in which such viruses could be more efficiently propagated.

Example 2

Cell Lines Containing EHV-VP16 Allow Enhanced Growth of HSV with an Inactivating Mutation in VP16

Experiments were performed to determine whether cell lines containing EHV-VP 16 could complement deficiencies in virus growth caused by mutations to the VP 16 gene which otherwise prevent efficient trans-activation of IE promoters and thus give poor virus growth.

BHK cells (grown in DMEM+10% FCS, both Gibco, at 37° C./5% CO2) were transfected (by the method of Gorman, 1985) in 10 cm plates with plasmids containing either only a neomycin (neo) resistance selectable marker gene (pcDNA3), or neo together EHV-VP16 under the control of a CMV promoter and BGHpA sequence (pcDNA3/E). After transfection, G418 (800 µg/ml; Gibco) was used to kill non-stably transfected cells and plates allowed to grow over. Cells were then trypsinised into 24 well plates to allow growth to be assessed with virus mutants and wild type control virus. This procedure allowed the 'average' effect on the mutants tested of the EHV-VP 16 gene and the control (neo only), without the clonal variation which would have occurred if colonies resulting from single transfectants had been cloned in each case. Results show the total virus yield/well 24 hrs after infection at a multiplicity of infection MOI of 0.01. Experiments were performed in duplicate either with or without the inclusion of HMBA (3 mM) in the media (MacFarlane et al., 1992).

Virus 17+ is a wild type virus, in 1814 contains an inactivating mutation in VP 16 (Ace et al. 1989), and virus 1764 contains the inactivating mutation in VP 16 together with deletion of both copies of ICP34.5, which does not itself significantly effect the growth of HSV in BHK cells (see Coffin et al., 1996).

Results:

| Virus under test | Plasmid transfected | Yield + HMBA | Yield − HMBA |
| --- | --- | --- | --- |
| 17+ | neo | 150000/250000 | 400000/250000 |
| in1814 | neo | 10000/15000 | 1000/1500 |
|  | EHV-VP16 | 200000/90000 | 80000/65000 |
| 1764 | neo | 35000/45000 | 5000/4500 |
|  | EHV-VP16 | 400000/300000 | 100000/250000 |

These results showed that EHV-VP 16 can complement the deficiency in virus growth caused by the inclusion of inactivating mutations in the gene for VP 16, such as in virus in1814 (Ace et al., 1989). Such viruses can be grown to near wild type levels, the level of complementation being greater than that achieved by the inclusion of HMBA in the media which has previously been reported to increase the efficiency of growth of HSV with mutations in VP 16 (MacFarlane et al., 1992).

Example 3

Cell Lines Containing EHV-VP16 and ICP27 Give Enhanced Growth of HSV Mutants Deficient in VP16 and ICP27

BHK cell lines prepared by the methods above were cloned out after transfection with only an ICP27 containing plasmid (the ICP27 coding sequence promoter and polyA excised from pSG130BS [Sekulovich et al 1988] with SacI and SphI inserted between the EcoRI and SalI sites in pPGKneo [Soriano et al 1991]) or the ICP27 containing plasmid together with pcDNA3/E. This showed that in most cases better growth (as assessed by growth curves) could be obtained of viruses deficient in both ICP27 and vmw65 (VP16; HSV1 mutant 1764/27-/pR20) using clones resulting from the dual transfection. These experiments also showed considerably larger plaques when HSV1 mutants inactivated for vmw65 (VP16), with or without deletion of ICP27, were grown on cells containing EHV gene 12.

Virus 1764/27-/pR20 contains an HSV1 LAT (nts 118, 866-120,219(PstI-BstXII)/CMV/lacZ cassette inserted so as to delete the entire ICP27 coding sequence, UL55, UL56 (both non-essential genes; Roizman, R. and A. Sears. 1996) and part of the LAT region in virus strain 1764 (Coffin et al, 1996) using flanking regions (nts 110,095-113,229) EcoRI-NdeI and 120,468-125,068 [HpaI-SacI] separated by a unique BglII site) and the selection and purification of X-gal staining plaques on B1310/2 cells (Howard et al, 1998).

Example 4

Promoter Choice Driving ICP4 is Important in the Generation of Cell Lines Giving Effective Growth of HSV Mutants Deficient in VP16, ICP27 and ICP4

Here cell lines capable of allowing the effective growth of viruses with VP16 deficiencies and in which both ICP27 and ICP4 were also deleted were generated.

We have found, as described above, that the ICP27 promoter driving ICP27 provides effective cell lines complementing viruses deleted for ICP27 when the cells also contain EHV gene 12. Thus it was anticipated that the ICP27 promoter might also provide optimal regulation of ICP4 in cells complementing VP16, ICP27 and ICP4. Hence cell lines were produced in which ICP4 under ICP27 promoter and poly-A control in a plasmid encoding phleomycin resistance (plasmid p27/4zeo) was transfected into cells which already effectively allowed the propagation of viruses which lacked ICP27 and were deficient in VP16 (cell lines generated in Example 3 above). Phleomycinlneomycin resistant colonies were picked and cloned out. However these were generally found to give only very poor growth of HSV-1 mutants deficient in VP16, ICP27 and ICP4 (virus 1764127-/4-/pR20.5), with only 5 out of 140 colonies picked giving significant growth. Plasmid p27/4zeo was constructed by replacing the ICP4 promoter in plasmid p4/2zeo (upstream of the BstEII site [HSV-1 nt 131,187]; see below) by a BamHI-DrdI (HSV-1 nts 113,322-113,728) promoter fragment from pSG130BS. The ICP4 Poly A sequence was replaced by removal of sequences after the MseI site (HSV-1 nt 127,167) which were replaced with an EcoNI-SacI (HSV-1 nts 115,267-115,743) fragment from pSG130BS, encoding the ICP27 poly A Sequence.

Virus strain 1764/27-/4-/pR20.5 was constructed by insertion of a cassette consisting of GFP (E-GFP; Clontech) and lacZ driven by CMV and RSV promoters respectively in a back-to-back orientation and separated by HSV-1 LAT sequences (PstI-BstXI as in Example 3) into ICP4 flanking regions (HSV-1 nts 123,459-126,774 [Sau3aI-Sau3aI] and 131,730-134,792 [SphI-KpnI] with nts 124,945-125,723 [NotI-NotI; encodes ICP34.5] deleted separated by unique XbaI and SalIII sites in plasmid pDICP4) and recombination into virus strain 1764/27-w (virus strain 1764/27-/pR20 with the lacZ insertion removed by recombination with empty ICP27 flanking regions) using B4/27 cells which complement both ICP27 and ICP4. X-gal staining/green fluorescent plaques were selected and further purified. Cell line B4/27 was prepared by co-transfection of pSG130BS, plasmid p4/2 (see below) and pMAMneo (Invitrogen) into BHK cells. Neomycin resistant clones were then selected.

Following these disappointing results other promoters were tested driving ICP4. Thus further phleomycin/neomycin resistant cell lines were produced in which ICP4 was driven either by the ICP4 promoter and poly A (using plasmid p4/2zeo) or by the dexamethasone inducible MMTV promoter and an SV40 poly A (using plasmid pMAMzeo/ICP4). Here it was hoped that either correct regulation of ICP4 expression by the ICP4 promoter or dexamethasone inducible ICP4 expression might provide cell lines capable of improved growth of HSV-1 mutants deficient for VP16, ICP27 and ICP4.

For construction of p4/2zeo a phleomycin resistance gene cassette was excised from plasmid pVgRxR (Invitrogen) as a BamHI fragment and inserted into the unique BglII site of plasmid p4/2 giving plasmid p4/2zeo. p4/2 contains the ICP4 promoter, coding region and polyA (HSV-1 nts 126, 764-131,730 [DdeI-SphI]) inserted into pSP72 (Promega). For construction of pMAMzeo/ICP4 the neomycin resistance gene (excised as a BamHII fragment) in plasmid pMAMneo (Invitrogen) was repalced by the phleomycin resistance gene as above, again as a BamHI fragment. The ICP4 coding region (HSV-1 nts 127,167-131,187 [MseI-BstEII]) was then inserted after the MMTV promoter at the XhoI site.

138 and 88 clones using the ICP4 and MMTV promoterrespectively were picked and virus growth characteristics analysed. Of the ICP4 promoter driven clones, the majority were of only limited permissivity for the VP 16/ICP27/ICP4 deficient virus, although two clones were capable of giving efficient growth. It was thought that this variability probably refleted positional effects altering the regulation of the ICP4 promoter in the context of EHV gene 12 expressing cells, in some rare cases allowing efficient growth of the VP 16/ICP27/ICP4 deficient virus. However of the clones picked in which ICP4 was controlled by the MMTV promoter, 60 out of 88 gave efficient growth, at least as good as growth on the two ICP4 promoter containing cell lines. This indicated that with the MMTV promoter positional effects are of minimal importance for effective ICP4 regulation in the context of EHV gene 12 containing cell lines, unlike when the ICP4 promoter is used. However, inclusion of dexamethasone in the media at the time of inoculation using cells containing ICP4 under MMTV promoter control did not increase the yield of the VP 16/ICP27/ICP4 deficient virus.

REFERENCES

Ace C I et al. (1988) *J. Gen. Virol.*, 69, 2595-2605.
Coffin R S and Latchman D S (1996). In: Genetic Manipulation of the Nervous System (DS Latchman Ed.) pp 99-114: Academic Press, London.
Ace C I et al. (1989) *J. Virol.*, 63, 2260-2269.
MacFarlane M, et al. (1992) *J. Gen. Virol.*, 73, 285-292.
Lewis J B, et al. (1997) *Virology*, 230, 369-375.
Misra V, et al. (1994) *J. Virol.*, 68, 4898-4909.
Moriuchi H, et al. (1993) *J. Virol.*, 67, 2739-2746.
Coffin R S, et al. (1996) *Gene Therapy*, 3, 886-891.
Gorman C M (1985) In: DNA cloning, a practical approac. Glover D M (Ed). IRL Press, pp 143-190.
Moriuchi H, et al. (1995) *J. Virol.*, 69,4693-4701.
Gelman I H and Silverstein S (1987) *J. Virol.*, 61, 2286-2296.
Samaniego L A et al. J. Virol. (1995); 69: 5705-5715
MacLean A R et al, (1991), *J Gen Virol* 72: 632-639.
Chou, J et al. (1994), *J. Virol.* 68: 8304-8311.
Chou J and Roizmann B (1992), *PNAS* 89: 3266-3270.
Rice, S A and Knipe D M. (1990), *J. Virol* 64: 1704-1715.
DeLuca N A et al. (1985), *J. Virol.*, 56: 558-570.
Lokensgard J R, et al. (1994) *J. Virol.*, 68, 7148-7158.
Smiley, J. R., and J. Duncan. 1997. J. Virol. 71: 6191-6193.
Soriano, P., C. Montgomery, R. Geske, and A. Bradley. 1991. Cell 64:693-702.
Sekulovich, R. E., K. Leary, and R. M. Sandri-Goldin. 1988. J. Virol. 62: 45104522.
Roizman, R. and A. Sears. 1996. In Fields, B. N., D. M. Knipe, and P. M. Howley (eds.), Fields Virology. Lippincott-Raven Publishers, Philadelphia.
Howard, M. K et al, 1998. Gene Therapy 5: 1137-1147.

The invention claimed is:

1. A process for propagating a mutant herpes simplex virus (HSV) comprising:
   (a) a mutation in its endogenous VP16 gene wherein the mutation reduces or abolishes the ability of the protein encoded by the VP16 gene to activate viral transcription without disrupting the structural activity of the protein; and
   (b) a heterologous gene;
   which process comprises infecting a cell line with the mutant herpes virus and culturing the cell line,
   wherein the cell line comprises a nucleic acid sequence from a non-HSV herpes virus encoding a functional equivalent of the HSV VP16 polypeptide operably linked to a control sequence permitting expression of the polypeptide in said cell line and wherein the nucleic acid sequence (i) complements the endogenous gene and (ii) does not undergo homologous recombination with the endogenous gene.

2. A process according to claim 1 wherein the functional equivalent of the HSV VP16 polypeptide is encoded by a herpes virus gene selected from a bovine herpes virus gene and an equine herpes virus gene.

3. A process according to claim 2 in which the herpes virus gene is equine virus gene is equine herpes virus 1 gene 12, or the bovine herpes virus gene BTIF.

4. A process according to claim 1 wherein the control sequence comprises a constitutively active promoter or an inducible promoter.

5. A process according to claim 1 wherein the HSV is an HSV-1 or HSV-2.

6. A process according to claim 1 wherein the mutant herpes simplex virus comprises additional mutations which functionally inactivate one or more additional endogenous genes of said virus and the cell line comprises additional nucleic acid sequences encoding functional herpes virus genes which complement said additional functionally inactive endogenous genes.

7. A process according to claim 6 wherein said additional nucleic acid sequences encode at least one of HSV-1 ICP27, HSV-1 ICP4, an equivalent of said HSV-1 ICP27 in HSV-2 or another herpes virus, and an equivalent of said HSV-1 ICP4 in HSV-2 or another herpes virus.

8. A process according to claim 7 in which at least one of said HSV-1 ICP27 or said equivalent is driven by the ICP27 promoter and said HSV-1 ICP4 or equivalent is driven by the MMTV LTR promoter.

9. A process according to claim 7 wherein said additional nucleic acid sequences additionally encode HSV-1 ICP27 or an equivalent thereof in HSV-2 or another herpes virus.

10. A process according to claim 9 wherein the HSV-1 ICP27 or equivalent thereof is driven by the ICP27 promoter.

11. A process according to claim 1 which the heterologous gene is operably linked to a control sequence permitting expression of the heterologous gene in a mammalian cell.

12. A process according to claim 1 wherein the heterologous gene is an HSV gene that is not operably linked to the viral control sequence with which it is naturally associated.

13. A process according to claim 1 wherein the heterologous gene encodes a polypeptide of therapeutic use.

* * * * *